(12) United States Patent
Baranov et al.

(10) Patent No.: US 7,135,296 B2
(45) Date of Patent: Nov. 14, 2006

(54) ELEMENTAL ANALYSIS OF TAGGED BIOLOGICALLY ACTIVE MATERIALS

(75) Inventors: Vladimir Baranov, Richmond Hill (CA); Scott Tanner, Aurora (CA); Dmitry Bandura, Aurora (CA); Zoe Quinn, Toronto (CA)

(73) Assignee: MDS Inc., Concord ( * ) Notice: Subject to any disclaimer, the term of this patent is extended or adjusted under 35 U.S.C. 154(b) by 0 days.

(21) Appl. No.: 09/905,907

(22) Filed: Jul. 17, 2001

(65) Prior Publication Data

US 2002/0086441 A1 Jul. 4, 2002

Related U.S. Application Data

(60) Provisional application No. 60/258,387, filed on Dec. 28, 2000.

(51) Int. Cl.
*G01N 33/53* (2006.01)
*A61K 51/00* (2006.01)

(52) U.S. Cl. .................. 435/7.1; 436/501; 424/1.49

(58) Field of Classification Search .............. 424/1, 424/1.5, 12, 1.49; 250/282, 303, 461 B; 23/230 B, 915, 920; 422/68, 73; 436/533, 436/534, 525, 526, 829, 501; 435/6, 7.1; 530/350; 536/23.1
See application file for complete search history.

(56) References Cited

U.S. PATENT DOCUMENTS

| | | | | |
|---|---|---|---|---|
| 4,022,876 | A | * | 5/1977 | Anbar ................... 436/542 |
| 4,205,952 | A | * | 6/1980 | Cais ...................... 436/518 |
| 4,313,734 | A | * | 2/1982 | Leuvering .............. 23/230 B |
| 4,411,993 | A | | 10/1983 | Gillis |
| 4,454,233 | A | | 6/1984 | Wang |
| 4,543,439 | A | | 9/1985 | Franckelton et al. |
| 4,637,988 | A | | 1/1987 | Hinshaw et al. |
| 4,902,614 | A | | 2/1990 | Wakabayashi et al. |
| 5,071,775 | A | * | 12/1991 | Snapka et al. ........... 436/545 |
| 5,521,289 | A | * | 5/1996 | Hainfeld et al. ......... 530/391.5 |
| 5,958,783 | A | | 9/1999 | Josel et al. |
| 6,140,638 | A | | 10/2000 | Tanner et al. |
| 6,242,735 | B1 | * | 6/2001 | Li et al. ................. 250/288 |
| 6,428,956 | B1 | * | 8/2002 | Crooke et al. ............ 435/6 |
| 6,746,679 | B1 | | 6/2004 | Nathoo |
| 6,770,266 | B1 | | 8/2004 | Santarpia, III et al. |
| 2002/0136929 | A1 | | 9/2002 | Zaidel et al. |
| 2003/0089886 | A1 | | 5/2003 | Montgomery |

FOREIGN PATENT DOCUMENTS

| | | | |
|---|---|---|---|
| WO | WO 99/45150 | * | 9/1999 |
| WO | WO 00/36136 | | 6/2000 |
| WO | WO02/054075 | | 7/2002 |

OTHER PUBLICATIONS

Schramel, P (CANAS '95, Colloquim Analytische Atomspektroskopie, Konstanz, Germany, Apr. 2-7, 1995(1996), Meeting Date 1995, 671-681, Abstract Only).*

C. Zhang et al., "Application of the Biological Conjugate between Antibody and Colloid Au Nanoparticles as Analyte to Inductively Coupled Plasma Mass Spectrometry," Analytical Chemistry, pp. 3.8, A-D, 2001.

International Search Report for PCT/CA 01/01815, dated Apr. 24, 2002.

Blake et al., "Immunoassays for Metal Ions," Analytica Cimica Acta 376, 1998, pp. 13-19.

Darwish et al., "One-Step Competitive Immunoassay for Cadmium Ions: Development and Validation for Environmental Water Samples," Analytical Chemistry, vol. 73, No. 8, Apr. 25, 2001, pp. 1889-1895.

Neilsen et al., "Laser Ablation Inductively Coupled Plasma-Mass Spectrometry in Combination with Gel Electrophoresis: A New Strategy for Speciation of Metal Binding Serum Proteins," Spectrochimica Acta Part B, vol. 53, No. 2, Feb. 1998, pp. 339-345.

Evans et al., "A Method for Characterization of Humic and Fulvic Acids by Gel Electrophoresis Laser Ablation Inductively Coupled Plasma Mass Spectrometry," The Royal Society of Chemistry, 2000, vol. 15, No. 2, Feb. 2000, pp. 157-161.

Zhang et al., "A Novel Combination of Immunoreaction and ICP-MS as a Hyphenated Technique for the Determination of Thyroid-Stimulating Hormone (TSH) in Human Serum," J. Anal. At. Spectrom, vol. 16, No. 12, Dec. 2001, pp. 1393-1396.

Baranov et al., "A Sensitive and Quantitative Element-Tagged Immunoassay with ICPMS Detection," Analytical Chemistry, vol. 74, No. 7, Apr. 1, 2002.

Binet, et al.; Detection of Zinc/Cadmium Binding Proteins in *Escherichia coli* By Gel Electrophoresis—Laser Ablation—Inductively Coupled Plasma—Mass Spectrometry; University of Sheffield, Krebs Institut for Biomolecular Research.

(Continued)

*Primary Examiner*—Long V. Le
*Assistant Examiner*—Lisa V. Cook
(74) *Attorney, Agent, or Firm*—Matthew Marquardt; MaryAnne Arnoldo; Torys LLP

(57) ABSTRACT

Improved methods for the detection and quantitation of labeled biological materials in a sample using elemental spectroscopic detection are described. Element-labeled biologically active materials, comprising antibodies, antigens, growth factors, hormones, receptors and other biologically active materials covalently attached to a stable elemental tag, can be used in specific binding assays and measured by elemental spectroscopic detection. Also described are methods for the determination of metals in samples of interest using specific antibodies to isolate the target metals and elemental spectroscopy for detection and quantitation.

27 Claims, 5 Drawing Sheets

OTHER PUBLICATIONS

Interscience Publishers; *Advanced Inorganic Chemistry*, pp. 528-530 (1972).
Köhler, et al.; *Nature*, vol. 256; pp. 495-497 (Aug. 7, 1975).
Wagenknecht, et al.; *Biophysical Journal*, vol. 67, pp. 2286-2295 (Dec. 1994).
Von Banchet & Heppelmann; *Journal of Histochemistry and Cytochemistry*, vol. 43, No. 8, pp. 821-827 (1995).
Wenzel & Baumeister; *Structural Biology*, vol. 2, No. 3, pp. 199-204 (Mar. 3, 1995).
Qiu & Song; *Analytical Biochemistry*, vol. 240, pp. 13-16 (1996).
De Llano, et al.; *Analytical Biochemistry*, vol. 243, pp. 210-217 (1996).
Korth, et al.; *Nature*, vo. 390, pp. 74-77 (Nov. 6, 1997).
Blake, et al.; *Analytica Chimica Acta* vol. 396, pp. 13-19 (1998).
Bordes, et al.; *Talanta*, vol. 48, pp. 201-208 (1999).
Tanner & Baranov; *J. Am Soc Mass Spectrom*, vol. 10, pp. 1083-1094 (1999).
Baranov & Tanner; *J. Anal. At. Spectrom*, vol. 14, pp. 1133-1142 (1999).
Chen, et al.; *Anal. Chem.*, vol. 72, pp. 1134-1143 (Feb. 15, 2000).
De Llano, et al.; *Anal. Chem.*, vol. 72, pp. 2406-2413 (Apr. 25, 2000).
Bandura, et al.; *J. Anal. At. Spectrom*, vol. 15, pp. 921-928 (Jul. 26, 2000).
Tanner, et al.; *J. Anal. At. Spectrom*, vol. 15, pp. 1261-1269 (Aug. 9, 2000).
Nagaoka & Maitani; *Analyst*, vol. 125, pp. 1962-1965 (Oct. 23, 2000).
Baldwin, et al.; *Journal of Biological Chemistry*, vol. 276, No. 11, pp. 7791-7796 (2001).
Wind, et al.; *Anal. Chem.*, vol. 73, pp. 29-38 (Jan. 1, 2001).
Laffling, et al.; *Neuroscience Letters*, vol. 300, pp. 99-102 (2001).
Darwish & Blake; *Analytical Chemistry*, vol. 73, No. 8, pp. 1889-1895 (Apr. 15, 2001).
Houk, Robert S., "Inductively Coupled Argon Plasma as an Ion Source for Mass Spectrometric Determination of Trace Elements," *Anal. Chem.*, 1980, 52, pp. 2283-2289.
Frieden, Earl, Lipsett, Mortimer B. and Winzler, RIchard J., "Methods for Labeling Thyroxine with Radioactive Iodine", Apr. 2, 1948, Science, vol. 107, pp. 353-354.
Horan, Paul K. and Wheeless, Jr., Leon L., "Quantitative Single Cell Analysis and Sorting", Science, Oct. 14, 1997, vol. 198, pp. 149-157.
Baranov V.I. A Dynamic Reaction Cell for Inductively Coupled Plasma Mass Spectrometry (ICP-DRC-MS). Part 1. The rf-field energy contribution in thermodynamics of ion molecule reactions. J. Anal. At. Spectrom. 14:1133-1142 1999.
P. A. Bartlett et al., "Synthesis of Water-Soluble Undecagold Cluster Compounds", J. Am. Chem. Soc. 100: 5085-5089, 1978.
Bartel et al., "Isolation of new ribozymes from a large pool of random sequences", Science 261:1411-1418 (1993).
F.A. Cotton et al., 1972, Advanced Inorganic Chemistry: A Comprehensive Text, "Introduction to the Transition Elements", Interscience Publishers, p. 528-554.
de Llano et al., "Electrothermal atomic absorption spectrometric diagnosis of familial hypercholesterolemia", Anal. Chem. 72, 2406-2413, 2000.
Ellington et al., "In vitro selection of RNA molecules that bind specific ligands", Nature 346(6287): 818-822 (1992).
Ellington et al., "Section in vitro of single-stranded DNA molecules that fold into specific ligand-binding structures", Nature 355(6363):850-852 (1992).
Robertson et al., "Selection in vitro of an RNA enxyme that specifically cleaves single-stranded DNA" Nature 344(6265):467-468 (1990).
Segond von Banchet et al., "Non-radioactive localization of substance P binding sites in rat brain and spinal cord using peptides labeled with 1.4 nm gold particles", J. Histochem. Cytochem. 43: 821-827, 1995.
Turek et al., "Systematic evolution of ligands by exponential enrichment: RNA ligands to bacteriophage T4 DNA polymerase" Science 249(4968):505-510 (1990).
Neilsen et al., Laser ablation inductively coupled plasma-mass spectrometry in combination with gel electrophoresis: a new strategy for speciation of metal binding serum proteins. Spectrochimica Acta Part B 53, Elsevier Science B.V., 1998, 339-345.
Marshall, J. et al. "Atomic Spectromety Update-Atomic Emission Spectrometry", Journal of Analytical Atomic Spectrometry, Jun. 1997, vol. 12 (263R-290R).
Lorsch, et al., "In vitro selection of RNA aptamers specific for cyanocobalamin", Biochem., 33(4): 973-982 (1994).
International Search Report for PCT/CA2004/000974.
Baranov, V. I. et al., "A sensitive and quantitative element-tagged immunoassay with ICPMS detection", Analytical Chemistry, Apr. 2002, vol. 74 No. 7, 1, 1629-1636.
Holmberg, R. C. et al., "Isolation of DNA aptamers that bind Ru(bby) 2phen2+", Abstracts of Papers American Chemical Society, vol. 224, No. 1-2, 2002 p. INOR105.
Hess, A. et al., "Transition metal labels on peptide nucleic acid (PNA) monomers", Chemical Communications, May 1999, United Kingdom, vol. 5, No. 10 May 1999 p. 8886.
Csaki, A. et al., "Gold nanoparticles as nove label for DNA diagnostics", Expert Review of Molecular Diagnostics, Mar. 2002, vol. 2, No. 2 Mar. 2002, p. 89-94.
Green, L. S. et al., "Aptamers as reagents for high-throughput screening", Biotechniques, Eaton Publighing, Natick, US, vol. 30, No. 5, May 2001, p. 1094-1095.

* cited by examiner

ELEMENTAL ANALYSIS OF TAGGED BIOLOGICALLY ACTIVE MATERIALS

CROSS-REFERENCE TO RELATED APPLICATIONS

Applicants claim the right of priority under 35 U.S.C. 119(e) based on U.S. Provisional Application Ser. No. 60/258,387 filed on Dec. 28, 2000.

FIELD OF THE INVENTION

Elemental Analysis of Tagged Biologically Active Materials

The present invention relates to methods for the detection and measurement of element tagged biologically active material and further relates to the detection and measurement of elements in a sample of interest. More particularly, the present invention is directed to detection and measurement of tagged immunoglobulins or antigens using an atomic mass or optical spectrometer having a source of atoms or atomic ions.

BACKGROUND OF THE INVENTION

Various methods are in use for the detection and measurement of biological materials. To date, these determinations are generally facilitated through the use of radiological, fluorescent or enzymatic tags. None of these methods have successfully dealt with elemental tagging of biologically active materials, and in particular immunoglobulins and antigens, followed by detection using atomic mass or optical spectrometry.

The methods used to date have included (1) elemental tagging in immunoassays, (2) elemental tagging using radioisotopes, (3) elemental tagging to enhance fluorescence, (4) immunological detection of elemental species without tagging, and (5) direct elemental tagging for cell uptake studies. We will review each of these areas in turn.

Elemental Tagging in Immunoassays

Wang 1984 (U.S. Pat. No. 4,454,233) disclosed the possibility of utilizing a mass spectrometer as a means of immunoassay detection. Wang's method required a cumbersome preliminary set of steps to first prepare a tagged 'mobile unit' which was then conjugated to an antibody/antigen. In the preferred embodiment, the 'mobile unit' was comprised of a latex particle embedded with heavy tagging elements such as Fe, Ni, Cu and Co. Among Wang's reasons for utilizing 'mobile units' were: (1) easy separation of bound reactant from unbound reactant, (2) simultaneous detection of many antigen/antibody complexes owing to the small size of mobile units, and (3) possible utilization of 'unstable' or 'reactive' tags, as tags embedded in the latex would not interfere with the reaction. However, due to the burdensome requirement of preparing mobile units, Wang's method was impractical and has not been used for immunoassay detection.

Immunoassay detection using element tagged immunoglobulins and antigens has also been possible using colloidal gold or extremely small beads of gold (several nanometers in diameter), for example NANOGOLD™ particles. Van Banchet and Heppelmann (1995), Wagenknecht et al. (1994), and Wenzel and Baumeister (1995) used colloidal gold to visualize protein structure in the cell and to detect receptor-ligand binding by electron microscopy. However, these assays suffer from lack of quantitation capabilities.

Element tagging has also been used in electrochemical immunoassays followed by polarographic detection of the generated complexes based on the catalytic conversion of a substrate by labeled metal ion or the anodic current of metal labeling Qiu and Song (1996). Similar to the preceding example, the assay lacked quantitation capabilities.

Thus, although elemental tagging has been used in immunoassays, the tagging methods have been cumbersome or were ineffective at quantitation.

Elemental Tagging Using Radioisotopes

Historically, the most common use of elemental tagging has been the use of radioactive elements. While radioassays remain the method of choice due to their exceptional sensitivity to low levels of analyte, their general use is limited by the restrictions in dealing with radioactive materials.

Elemental Tagging to Enhance Fluorescence

Recently, elemental tagging has been used to enhance luminescence of fluorescent tags. U.S. Pat. No. 4,637,988 to Hinshaw et al., describes the use of lanthanide metals complexed with fluorescent compounds and chelating agents, that can be used in specific binding assays. U.S. Pat. No. 5,958,783 to Josel et al. describes the use of metal complexes with a charged linker as luminescent groups in fluorescence-based or electrochemiluminescence-based assays.

However, these fluorescent tagging methods suffer from the disadvantages associated with their relatively low sensitivity and resulting problems with quantitative analysis in samples containing low concentrations of target molecules. As well, fluorescence-based methods are limited to the analysis and quantification of only one or at most a few target substances per assay.

Immunological Detection of Elemental Species

Blake et al. (1998) and Darwish and Blake (2001) disclosed a method of detection and quantitation of elemental species by complexing elemental species with antibodies that recognize chelated elemental species, using antibodies conjugated with fluorescent tags. However, as outlined above, fluorescence based assays suffer from low sensitivity and are limited to one or a few targets per assay.

Direct Elemental Tagging in Conjunction with Gel Electrophoresis

Binet et al. (2001) disclosed a method of determining untagged proteins by separation using gel electrophoresis, followed by laser ablation of the separated spots and detection using mass spectrometry. However, this method is limited to molecules that are naturally detectable by spectrometry.

Wind et al. (2001), Nagaoka and Maitani (2000) and Baldwin et al. (2001) used chromatography to separate proteins, followed by detection using mass spectrometry. Similarly, Chen et al, 2000 incorporated isotopic tags of 13C, 15N and 2H in proteins before chromatographic separation and detection using organic mass spectrometry. However, separation with chromatography is an added step, which can be onerous.

Thus, if one does not tag, one is limited to what is being assayed and using chromatography for separation adds a step to the process.

Direct Elemental Tagging for Cell Uptake Studies

De Llano et al.(1996) and de Llano et al. (2000), disclosed a method of visualizing and measuring the uptake of low density lipoprotein (LDL) tagged with colloidal gold by cells using electron microscopy and mass/atomic spectrometry. However, the biological material was labeled directly and gel electrophoresis was not utilized.

Thus, various methods have been developed for visualizing and analyzing element tagged biologically active compounds. However, they have innate limitations, ranging from handling radioactive waste, to low sensitivity with fluorescence based assays, to detection only capabilities, and to cumbersome preparation or separation steps.

An enormous potential exists for the development of very simple biological assays that take advantage of capabilities offered by elemental tagging coupled with elemental detection using a mass or optical spectrometer. Mass and optical spectrometry offer high sensitivity, accurate quantitation and a wide dynamic range. The use of elements to label biologically active material allows construction of an enormous number of distinguishable tags.

This invention involves bridging the science of biology, and in particular immunology, and analytical atomic mass spectrometry. The invention offers an easy and simple means of tagging biological molecules. Further, it offers excellent detection capabilities, equaling (or surpassing) the sensitivity of radioassays. It offers the safety of florescent based assays, and the added feature of an enormous number of available tags, with the possibility of simultaneous detection of numerous biological complexes. In addition, the handling of the reacted tagged complexes can be crude, as the integrity of the chemical complex need not be preserved in assaying the element.

SUMMARY OF THE INVENTION

The last two decades have seen the improvement of elemental analysis due to the development of the inductively coupled plasma (ICP) source using mass or optical spectrometry. This has resulted in ultra sensitive spectrometers with high matrix tolerance and means of resolving isotopic and spectral interferences. The present invention has coupled the developments in this field with the continuing need to provide rapid and precise detection and measurement in biological assays.

In its broad aspect, the present invention provides a simple method of tagging biologically active materials, and detecting and measuring the reactant complexes by an atomic mass or optical spectrometer. Variations of the invention include detection and measurement of elemental species by complexing antibodies to chelated elemental species, and detection and quantitation of an analyte by tagging the analyte directly.

In addition, the present invention allows one to use a large array of elemental tags to allow the simultaneous or sequential detection and measurement of biologically active material. This is known as "multiplexing".

According to one aspect of the present invention, there is provided a method for the detection and measurement of a transition element in a sample, where the measured transition element is a tag on a biologically active material that binds with one of an analyte and analyte complex, comprising: i) combining the tagged biologically active material with one of the analyte and analyte complex, where the tagged biologically active material binds with one of the analyte and analyte complex, ii) separating bound tagged biologically active material from unbound tagged material, and iii) detecting and measuring the bound tag elements by one of an atomic mass and optical spectrometer having a source of ions or atomic ions. Variations of this method include a step of electrophoresis of one of the analyte and analyte complex. The analyte complex includes, but is not limited to, a primary antibody and an analyte or a primary antibody, secondary antibody and an analyte.

According to another aspect of the present invention, there is provided a method for the detection and measurement of an element in a sample, where the measured element is a tag on a biologically active material that binds with one of an analyte and analyte complex, comprising: i) combining the biologically active material with one of the analyte and analyte complex, wherein the biologically active material binds a transition element, ii) introducing the transition element to the sample, and iii) detecting and measuring the element by one of an atomic mass and optical spectrometer having a source of ions or atomic ions. Variations of this method comprise the step of electrophoresis of one of the analyte and analyte complex bound to the biologically active material. In a further variation, the step of combining the biologically active material and the analyte comprises cell transfection.

According to another aspect of the present invention, there is provided a method for the detection and measurement of an element of an elemental species in a sample, where an antibody specific to a chelated elemental species binds to the chelated elemental species, comprising: i) chelating the elemental species, ii) introducing the antibody into the sample, iii) separating the antibody bound chelated elemental species complexes from the sample, and iv) detecting and measuring an element of the elemental species contained in the removed complexes by one of an atomic mass and optical spectrometer having a source of atoms or atomic ions. Variations of this aspect include tagging the antibody with a transition element. A further variation includes, detection of the element of the elemental species, detection of the element of the tagged antibody, or both.

According to another aspect of the present invention, there is provided a method for the detection and measurement of an element in a sample, where the measured element is a tag on an analyte in a sample, comprising: i) tagging the analyte with a transition element, ii) electrophorescing the sample containing the tagged analyte, and iii) detecting and measuring the element by one of an atomic mass and optical spectrometer having a source of atoms or atomic ions.

According to a preferred aspect of the present invention, there is provided a method of measurement and detection of any of the aspects described above wherein the tagged biologically active material is a commercially available product.

According to another preferred aspect of the present invention, there is provided a method of measurement and detection of any of the aspects described above wherein the source of atoms or atomic ions is selected from a group consisting of inductively coupled plasma, graphite furnace, microwave induced plasma, glow discharge, capacitively coupled plasma, electrospray, MALDI and corona.

According to another preferred aspect of the present invention, there is provided a method of measurement and detection of any of the aspects described above wherein the source of atoms or atomic ions is an inductively coupled plasma source.

According to another preferred aspect of the present invention, there is provided a method of measurement and detection of any of the aspects described above wherein the element is an isotope or ion.

According to another preferred aspect of the present invention, there is provided a method of measurement and detection of any of the aspects described above wherein the element is selected from a group consisting of the noble metals, lanthanides, rare earth elements, gold, silver, platinum, rhodium, iridium and palladium.

According to another preferred aspect of the present invention, there is provided a method of measurement and detection of any of the aspects described above wherein the step of tagging comprises covalently coupling the element to one of the biologically active material and analyte.

According to another preferred aspect of the present invention, there is provided a method of measurement and detection of any of the aspects described above wherein the biologically active material is selected from a group consisting of an antibody, antigen, hormone, growth factor, receptor, protein, nucleic acid, virus and prion.

According to another preferred aspect of the present invention, there is provided a method of measurement and detection of any of the aspects described above wherein the tag is selected from the group consisting of a plurality of elements, a plurality of isotopes, a plurality of atoms of an isotope, a different number of atoms of each isotope and combinations thereof.

According to another preferred aspect of the present invention, there is provided a method of measurement and detection of any of the aspects described above comprising an additional step of introducing two or more biologically active materials or analytes having distinguishable elemental tags into a sample of interest for simultaneous determination. Further, the tag is selected from the group consisting of a plurality of elements, a plurality of isotopes, a plurality of atoms of an isotope, a different number of atoms of each isotope and combinations thereof.

According to another preferred aspect of the present invention, there is provided a method of measurement and detection of any of the aspects described above comprising an additional step of sample introduction to one of the atomic mass and optical spectrometer, wherein the sample introduction includes laser ablation. Laser ablation is selected from the group consisting of laser ablation of polyacrylamide gels, laser ablation of agarose gels, laser ablation of animal tissue samples and laser ablation of cell cultures. Further, laser ablation of polyacrylamide or agarose gels containing biologically active materials or analytes is tagged with an element selected from the group consisting of at least one element and at least one element having an unnatural composition.

According to an aspect of the present invention, there is provided a system of measurement and detection of any of the aspects described above.

According to an aspect of the present invention, there is provided the use of one of an atomic mass and optical spectrometer for the detection and measurement of the element of any of the aspects described above.

According to an aspect of the present invention, there is provided use of one of an atomic mass and optical spectrometer for the detection and measurement of the elemental species of any of the aspects described above.

Other features and advantages of the present invention will become apparent from the following detailed description. It should be understood, however, that the detailed description and the specific preferred embodiments of the invention are given by way of illustration only, since various changes and modifications within the spirit and scope of the invention will become apparent to those skilled in the art from this detailed description.

DETAILED DESCRIPTION OF THE FIGURES

The invention will now be described in relation to the drawings in which

DETAILED DESCRIPTION OF THE INVENTION

Definitions

Figure 1:
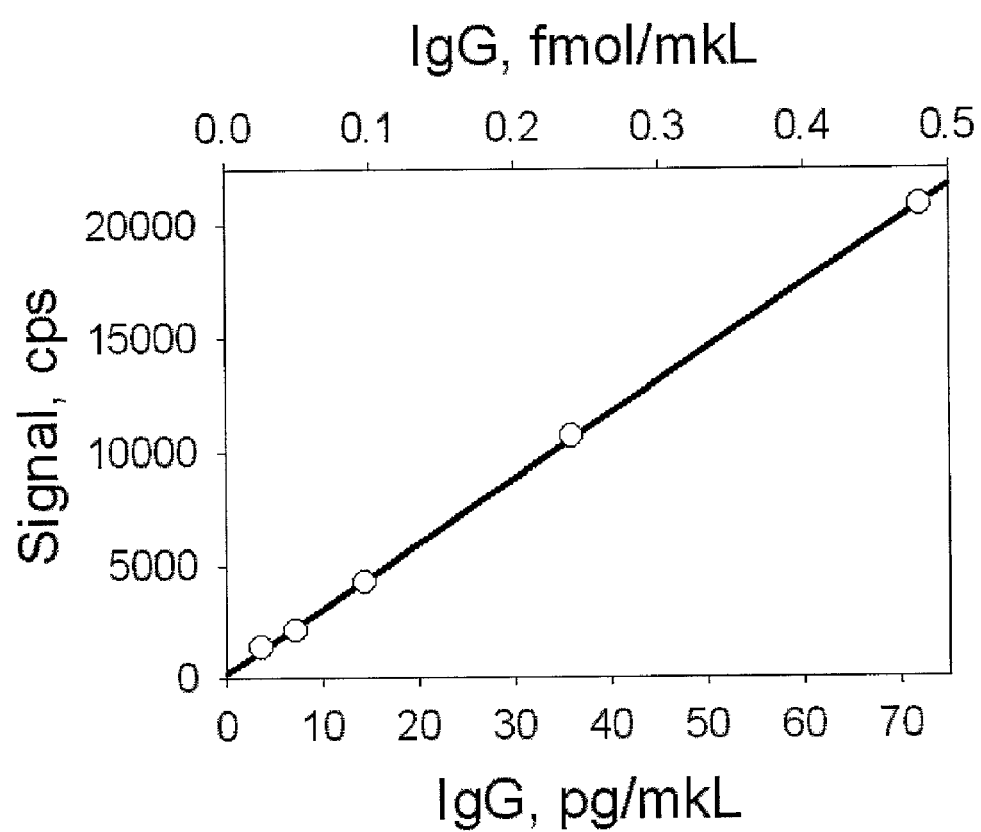
FIG. 1 is a graph illustrating a calibration curve obtained by dilutions of human IgG and immunoreaction with the gold-labeled antihuman antibody with detection and quantitation using ICP-MS.

As used in this application:

"analyte" means any substance being identified and measured in an analysis, and includes but is not limited to elemental species, element species chelate complexes; cells, viruses, prions, subcellular particles; proteins including more specifically antibodies, antigens, immunoglobulins, lipoproteins, glycoproteins, peptides, polypeptides; nucleic acids including DNA and RNA; and including peptidic nucleic acids; oligosaccharides, polysaccharides, lipopolysaccharides; cellular metabolites, haptens, hormones, growth factors, receptors, ligands, pharmacologically active substances, alkaloids, steroids, vitamins, amino acids and sugars.

"analyte complex" means an analyte bound to other molecules or biologically active materials. Examples of analyte complexes include, but are not limited to, complexes comprising a primary antibody and an analyte, and complexes comprising a primary antibody, a secondary antibody and an analyte.

"animal" means all members of the animal kingdom.

"atomic mass spectrometer" means a mass spectrometer that generates atomic ions, and detects atomic ions based on the mass/charge ratio.

"biologically active material(s)" means any biological substance found in nature and includes cells, viruses, prions, subcellular particles; proteins including more specifically antibodies, antigens, immunoglobulins, lipoproteins, glycoproteins, peptides, polypeptides; nucleic acids including DNA and RNA, and including peptidic nucleic acids; oligosaccharides, polysaccharides, lipopolysaccharides, cellular metabolites, haptens, hormones, growth factors, receptors, ligands, pharmacologically active substances, alkaloids, steroids, vitamins, amino acids and sugars.

"capacitively coupled plasma" (CCP) means a source of ionization in which a plasma is established by capacitive coupling of radiofrequency energy at atmospheric pressure or at a reduced pressure (typically between 1 and 500 Torr) in a graphite or quartz tube "corona" means a source of ionization in which a conductor (typically a needle) is provided a voltage relative to a counter electrode surface (typically containing an ion sampling aperture) such that the voltage gradient exceeds a critical value to cause ionization of the surrounding gas, but not sufficient to cause sparking.

"elemental species" means a molecule containing a metal bound to another atom or group of atoms. For example, selenite ($SO_3^{-2}$), selenate ($SO_4^{-2}$), methylselenocysteine and selenomethionine are elemental species of selenium.

"element tagged" means a molecule tagged with a transition element, including a noble metal or lanthanide.

"elemental tag" means any transition element, including a noble metal or lanthanide, used to tag the biologically active material or analyte.

"electrospray" means a source of ionization in which a liquid sample is nebulized from a tube due to the sufficiently high potential applied, which also provides a charge to the droplet, and in which the resultant charged droplet evaporates and fragments yielding small charged droplets or charged molecular ions.

"Fab" means the antigen binding fragment of an antibody obtained by papain reaction with immunoglobulin.

"Fab'" means the antigen binding fragment of an antibody. Fab' is obtained by pepsin reaction with immunoglobulin, followed by cleavage of two disulfide bonds.

"Glow discharge" (GD) means a source of ionization in which a discharge is established in a low pressure gas (typically between 0.01 and 10 Torr), typically argon, nitrogen or air, by a direct current (or less commonly radiofrequency) potential between electrodes.

"graphite furnace" means a spectrometer system that includes a vaporization and atomization source comprised of a heated graphite tube. Spectroscopic detection of elements within the furnace may be performed by optical absorption or emission, or the sample may be transported from the furnace to a plasma source (e.g. inductively coupled plasma) for excitation and determination by optical or mass spectrometry.

"inductively coupled plasma" (ICP) means a source of atomization and ionization in which a plasma is established in an inert gas (usually argon) by the inductive coupling of radiofrequency energy. The frequency of excitation force is in the MHz range.

"lanthanide" means any element having atomic numbers 58–71. They are also called rare earth elements.

"MALDI" means a source of ionization (Matrix Assisted Laser Desorption Ionization) in which ions are produced from a sample mixed with a matrix (typically analyzed in crystalline form) by exposure to laser irradiation, typically at low pressure "mass spectrometer" means an instrument for producing ions in a gas and analyzing them according to their mass/charge ratio.

"microwave induced plasma" (MIP) means a source of atomization and ionization in which a plasma is established in an inert gas (typically nitrogen, argon or helium) by the coupling of microwave energy. The frequency of excitation force is in the GHz range.

"multiplexing" means using more than one elemental tag for the simultaneous or sequential detection and measurement of biologically active material.

"noble metal" means any of several metallic elements, the electrochemical potential of which is much more positive than the potential of the standard hydrogen electrode, therefore, an element that resists oxidation. Examples include palladium, silver, iridium, platinum and gold.

"optical spectrometer" means an instrument calibrated to measure either wavelength of light or the refractive index of a prism, and includes atomic emission and atomic absorption spectrometers.

"plasma source" means a source of atoms or atomic ions comprising a hot gas (usually argon) in which there are (approximately) equal numbers of electrons and ions, and in which the Debye length is small relative to the dimensions of the source.

"rare earth metals" means any element having atomic numbers 58–71. They are also called "lanthanides".

"sample" means any composition of liquid, solid or gas containing or suspected of containing an analyte.

"transition element" means any element having the following atomic numbers, 21–29, 39–47, 57–79, and 89. Transition elements include the rare earth elements, lanthanides and noble metals. (Cotton and Wilkinson, 1972, pages 528–530).

There are a number of aspects to the present invention.

The first aspect involves a biologically active material which binds to an analyte in a sample. The biologically active material is tagged with a transition element. Most often, the biologically active material would be an immunoglobulin or antigen. The element is detected by an atomic mass or optical spectrometer having a source of atoms or atomic ions. Examples 1, 2, 3, 4, 5, 6, 7, 8, 10, 14, 15 and 16 describe this aspect of the invention in more detail.

The individual steps involved in this first aspect of the invention are known to those skilled in the art but the coupling of immunoassays with spectrometry is new and inventive. Each of the individual steps is described in Materials and Methods section of this application.

The benefits of this aspect of the invention are that: (1) it allows for the detection of minute quantities of analyte, (2) it allows for multiplexing, saving time, resources and providing for a better analysis of the sample, (3) the analysis is very rapid as there is no need to wait for enzymatic reactions, and measurement time by ICP-OES/MS is shorter than radiological tag measurement, (4) it has a large dynamic range, (5) radioisotopes are not required, producing a safe work environment and avoids toxic waste, and (6) the reacted complex does not need to be preserved, allowing the use of acidic media to degrade the complex and stabilize the element in solution and thereby increasing the period of storage of the sample before analysis.

The second aspect involves the determination of elemental species. In cases where mass spectrometry can not differentiate elemental species, the use of antibodies to detect elemental species coupled with mass spectrometry allows for their differentiation. Examples 11, 12 and 13 describe this aspect of the invention in more detail. In this aspect, as show in Example 13, multiplexing can be used. Again, the benefits of this aspect are that: (1) it allows for the detection of minute quantities of analyte, (2) it allows for multiplexing, (3) the analysis is very rapid, (4) there is a large dynamic range, (5) one can avoid the use of radioisotopes, (6) the reacted complexes do not need to be preserved, and (7) chromatographic separation is not required, which speeds up and simplifies the analysis.

The third aspect is the direct labeling of the analyte. The individual steps involved in this third aspect are known to those skilled in the art, but direct labeling coupled with mass spectrometry is new and inventive. Example 17 describes this third aspect of the invention. A variation of this aspect is described in Example 9. Again, the benefits of this third aspect are that: (1) it allows for the detection of minute quantities of analyte, (2) it allows for multiplexing, (3) the analysis is very rapid, (4) there is a large dynamic range, (5) one can avoid the use of radioisotopes, (6) the reacted complexes do not need to be preserved, and (7) chromatographic separation is not required, which speeds up and simplifies the analysis.

For all aspects of the invention, it is understood that the biologically active material can be added to the analyte, or the analyte can be added to the biologically active material. Further, an analyte complex can be formed, by the binding of molecules to the analyte, as seen in the examples outlined below, in which a series of antibodies (primary, secondary, tertiary) can be conjugated to the analyte forming an analyte complex.

Tagging Elements

The choice of the element to be employed in the methods of the present invention is preferably selected on the basis of its natural abundance in the sample matrix under investigation. In order to achieve selectivity, specificity, the ability to provide reproducible results, and include appropriate standards for accurate quantitation, it is evident that the tagging element should be of low natural abundance. For example, in a preferred embodiment, the rare earth elements or gold can be used as tag materials. Yet, in another embodiment, an unusual isotope composition of the tag can be used in order to distinguish between naturally present elements in the sample and the tag material. In this case non-radioactive isotopes of, for example, iron, potassium, nickel or sodium can be successfully distinguished from naturally abundant isotopes employing the elemental analysis.

The size of an elemental tag (ratio of atoms which are detectable by means of the elemental analysis to the biologically active material conjugate) may be varied in order to produce the most consistent, sensitive and quantitative results for each particular analysis.

In a preferred embodiment of this invention, several conjugates can be used in one sample simultaneously providing that the tagging material was selected to be different in every assay. In this embodiment the preferred ICP-MS technique is used in order to quantify different tagging elements simultaneously or sequentially depending on the apparatus employed.

Although many applications of the present method will involve the use of a single elemental tag for each biologically active material or analyte, it should be readily appreciated by those skilled in the art that the biologically active material or analyte may be tagged with more than one element. As there are more than 80 naturally occurring elements having more than 250 stable isotopes, there are numerous elements, isotopes and combinations thereof to choose from. For example, there are 20 distinguishable 3-atom tags that may be constructed from only 4 different isotopes, and one million distinguishable 15-atom tags that may be constructed from 10 different isotopes, or 70-atom tags that may be constructed from 5 different isotopes. Within limits prescribed by the need to have distinguishable tags when in combination, this will allow for simultaneous detection of numerous biologically tagged complexes. It is advantageous if the relative abundance of the tag elements is sufficiently different from the relative abundance of elements in a given sample under analysis. By "sufficiently different" it is meant that under the methods of the present invention it is possible to detect the target biologically active material or analyte over the background elements contained in a sample under analysis. Indeed, it is the difference in inter-elemental ratios of the tagged biologically active material or analyte, and the sample matrix that can be used advantageously to analyze the sample.

It is feasible to select elemental tags, which do not produce interfering signals during analysis. Therefore, two or more analytical determinations can be performed simultaneously in one sample. Moreover, because the elemental tag can be made containing many atoms, measured signal can be greatly amplified.

Detection of Metal Ions and Elemental Species

As was indicated above, an important application of the method of the present invention is the detection of metal in samples, such as toxic metals in environmental settings, including organisms, animals, and humans. Preferably, the invention detects metals in environmental settings. However, as is readily apparent to those skilled in the art, the toxicity of metals depends on the oxidation state, and often on the chemical structure of the elemental species. While an elemental detector, such as uses an ICP source, is able to determine the total quantity of an element in a sample it is generally unable to distinguish different species. There is an ongoing attempt to use different forms of chromatography to pre-separate the sample before the ICP, but this approach has been plagued with concern about the integrity of the sample, i.e., preservation of the oxidation state during sample preparation. The method of the present invention provides a means by which a long-standing problem of detecting speciation is overcome.

In a further embodiment of the present invention, there is provided a method of determining the concentration of a metal ion of interest, preferably toxic metals, more preferably in environmental/biological samples, comprising preparing an antibody which is specific to a selected speciation state of a given toxic metal, reacting said antibody with a solution suspected of containing a toxic metal, and detection of the resulting complexes by application of ICP-MS. Methods for the preparation of an antibody which is specific to a selected oxidation state of a given toxic metal are known by those skilled in the art and are described, for examples, in Bosslet et al.(1999), Blake et al. (1998), and Bordes et al. (1999).

In a further embodiment of the present invention, a tagged antibody is added to a sample containing a speciated element. The sample is split into two halves. The first half of the sample is analyzed for total speciated element. In the second half of the sample, the reacted complexes are separated from the unreacted. The tagging element and the speciated element are quantified in the reacted sample. The speciated element is also quantified in the unreacted sample. In this instance, the results will provide complementary data, and the fraction of the specific species in question will be determined.

As was also indicated above, an important application of the method of the present invention is the detection of elements of tags in samples by means of laser ablation of polyacrylamide gels where tagged molecules are separated by electrophoresis. This application can be used in order to analyze biomolecules in gels rapidly without destroying the sample. Also, by employing microablation it is feasible to distinguish cancerous cells from normal cells on histological section of biopsy samples using element-tagged antibodies specifically attached to the markers of cancerous populations.

The following section describes the methods and materials required to carry out the following invention.

METHODS AND MATERIALS

ICP-MS Techniques

Techniques using ICP-MS or OES can be applied for the purposes of this invention.

For example, in its latest realization it was described in Tanner el al.(2000a), Baranov et al. (1999), Tanner et al. (1999), Tanner et al. (2000b), and Bandura et al. (2000). This successful modification of ICP-MS includes the dynamic reaction cell, which is used in order to reduce isobaric interferences in atomic mass spectrometry. Briefly, the ICP-DRC-MS technique comprises a high temperature plasma in which the sample particles are atomized and ionized; vacuum interface which is designed to transport the plasma together with analyte ions from atmospheric pressure to vacuum; ion focusing optics; the dynamic reaction cell for chemical modification of the ion current and mass analyzing devise (quadrupole, TOF or magnetic sector). The sample is usually introduced to the plasma as a spray of droplets (liquid sample) or flow of particles (laser ablation of solid surfaces).

Sources of Atoms and Atomic Ions

The source of atoms or atomic ions can be produced from the following sources: inductively coupled plasma (ICP), graphite furnace, microwave induced plasma (MIP), glow discharge (GD), capacitively coupled plasma (CCP), electrospray, MALDI or corona.

Antibody Preparation

According to a preferred embodiment of the methods of the present invention, elementally tagged antibodies, or antibodies directed to a metal of interest are employed. Antibodies that bind a target of interest can be prepared using techniques known in the art such as those described by Kohler and Milstein (1975), Wakabayashi et al. (1990), Frackelton et al. (1985) and Gillis (1983), which are incorporated herein by reference. (See also Kennett, McKearn, and Bechtol (1980), and Harlow and Lane (1988), which are also incorporated herein by reference).

Within the context of the present invention, antibodies are understood to include monoclonal antibodies, polyclonal antibodies, antibody fragments (e.g., Fab, and F(ab')$_2$) and recombinantly produced binding partners. Antibodies are understood to be reactive against the target antigen if they bind to the target with an affinity of greater than or equal to $10^{-6}$ M.

Tagging of Biologically Active Materials

Preferably, the tagging element is in the form of a nanoparticle, which is attached to a biologically active material or analyte, such as for example an antibody, without degrading its activity (tagged conjugate). Examples of techniques for coupling elemental tags to biologically active materials are well known to those skilled in the art. For example, Barlett, P. A. et al. (1978), describe a metal cluster compound (Au$_{11}$) having a core of 11 gold atoms with a diameter of 0.8 nm. The metal core of 11 gold atoms in the undecagold metal cluster compound is surrounded by an organic shell of PA$_{r3}$ groups. This metal cluster compound has been used to form gold immunoprobes, for example, by conjugating Au$_{11}$ to Fab' antibody fragments as well as other biological compounds.

Another metal cluster compound which has been used as a probe is NANOGOLD™. NANOGOLD™ has a metal core with 50–70 gold atoms (the exact number not yet being known but believed to be 67 gold atoms) surrounded by a similar shell of organic groups (PA$_{r3}$) as undecagold. The metal core of NANOGOLD™ is 1.4 nm in diameter.

A more recent description of techniques for the preparation of biological tags which may be used in the method of the present invention is found in Hainfeld et al. (1996) (U.S. Pat. No. 5,521,289). Briefly Hainfeld et al (1996) describes, among others, thiol gold clusters produced by forming an organic-gold complex by reacting a compound containing a thiol with gold in solution. A second equivalent is also added of the thiol compound. Finally the gold organic is reduced with NaBH$_4$ or other reducing agents and organometallic particles are formed. These have the general formula Au$_n$ R$_{.m}$ R'$_I$ . . . , where n, m, and I are integers, R and R' are organic thiols, (e.g., alkyl thiols, aryl thiols, proteins containing thiol, peptides or nucleic acids with thiol, glutathione, cysteine, thioglucose, thiolbenzoic acid, etc.). With two equivalents of organic thiol compound, clusters with gold cores ~1.4 nm are formed with many organics. The organic moiety may then be reacted by known reactions to covalently link this particle to antibodies, lipids, carbohydrates, nucleic acids, or other molecules to form probes. Mixtures of organic thiols may be used to provide mixed functionality to the clusters. These organo-gold clusters are stable to heating at 100 degrees C.

The inventors believe that these organic thiol-gold preparations may also be made using similar processes with alternative metals to gold, e.g., platinum, silver, palladium and other metals, or mixtures of metal ions, e.g., gold and silver, resulting in mixed metal clusters. The metal clusters together with all other components of a sample are readily atomized and ionized in the high temperature ICP for subsequent MS or OES analysis.

Separation Techniques

According to one embodiment of the present invention, a tagged conjugate may be isolated for analysis by employing a filtration technique. For example, after incubation of an antigen with the tagged conjugate the sample undergoes filtering through a size separating centrifugal filter. Non-reacted tagged antibody together with other components of the sample mixture including non-reacted antigen pass into the filtrate. Complexes of antigen and antibody conjugate are left on the filter and after washing out can be stabilized in acidic solution. Since the integrity of the sample (i.e. the chemical form) is not important after separation, the separated sample can be acidified/degraded/stabilized (for example in acidic media) and quantitative analysis is preferably carried out using the ICP-MS technique. The optimal concentrations of all reagents for each system should be determined in an initial criss-cross serial dilution experiment and the concentration of reagent being quantitated must lie within the dynamic range of the standard curve. As will be readily apparent to those skilled in the art, other techniques of separation of free substance or non-complexed proteins from complexed substance may be used, for examples, salting out, chromatography, electrophoresis, gel filtration, fractionation, absorption, polyacrylamide gel electrophoresis, agglutination, or combinations thereof.

In light of the present disclosure, those skilled in the art will readily appreciate other methods and applications of the methods of the present invention.

The examples below are non-limiting and are merely representative of various aspects and features of the present invention.

EXAMPLES

Example 1

Nanogold™ Immunoassay

The following provides an example of the methods of the invention using the NANOGOLD-IgG™ (or NANOGOLD-FAB'™; Nanoprobes) immunoassay and its protocol. PBS buffer A is prepared as follows: 150 mM NaCl; 20 mM phosphate, pH 7.4; 1% BSA (bovine serum albumin). All eppendorf tubes, micro-titer plates, and filters to be used subsequently are pacified with PBS buffer A for 1 hour at room temperature. This treatment will reduce the non-specific interactions that occur between the plastic used and the antigen and NANOGOLD-IgG™. Alternatively low retention plastic products can be used (e.g. Axygen tubes). Following this a solution of the antigen (peptide, protein, etc.) in the concentration range of 1000 to 0.5pg/µl in PBS buffer A is prepared. All dilutions are stored on ice. Subsequently, 100 µl of either antigen solution or PBS buffer A (for controls) is pipetted into the individual wells of the micro-titer plate (or set of eppendorf tubes). The NANOGOLD-lgG™ is pre-filtered through 300 KDa (MICRCON™ or CENTRICON™) centrifugal filter devices. Dilutions of filtered NANOGOLD-IgG™ in PBS buffer A are prepared as follows: A 1:50 dilution is produced by adding 60 µl of NANOGOLD-IgG™ in 2940 µl PBS buffer A. A 1:500 dilution is then produced by adding 100 µl of NANOGOLD-IgG™ to 900 µl of PBS buffer A. Depending on concentration range of antigen, 100 to 500 µl of 1:500 NANOGOLD-IgG™ is then added to the wells of the plate and then incubated for 1–2 hours at room temperature. The total amount of antigen- NANOGOLD-IgG™ mix is then pipetted into the sample reservoir (upper chamber) of a 300 KDa MICROCON™ centrifugal filter device (max volume 2 ml). This sample is centrifuged at 14,000 g for 15 minutes at room temperature. The assembly is removed from the centrifuge and the vial separated from sample reservoir. The sample reservoir is inverted in a new vial, and spun for 3 minutes at 1000 g to transfer the concentrate to a new vial. Finally, a fixed volume of the collected antigen-NANOGOLD-IgG™ antibody mixture is diluted to 1 ml with 10% HCl/1 ppblr for stabilization. Ir provides an internal standard for ICP-MS quantitation and the acid solution is suitable for the elemental analysis. The linearity of the ICP-MS detector response as a function of the concentration of the analyte human IgG is shown in the results presented in FIG. 1.

Example 2

Immunoassay, other than NANOGOLD-IgG™

According to this example, an antibody is tagged with an element (eg. Eu, Ru, etc.) suitable for analysis by ICP-MS and is introduced into a sample containing antigens of interest (e.g. human blood proteins). The element-tagged antibody reacts specifically to the target antigen. The resulting tagged antigen-antibody complex is separated from un-reacted antibody (as in Example 1, 3, 4, 5, 8, 9, or 10), and the tagged complex is analyzed by ICP-MS. Variations of this example include:
  a) Tagging with multiple atoms to amplify the signal and thereby improving detectability.
  b) As, a), except the tag contains several isotopes of the same element or different elements, preferably in a non-natural (unusual) distribution, so that the unique isotope distribution is a determinant of the targeted antigen. It is to be recognized that there are more than 80 naturally occurring elements (of which some 60 may have value in this application) having more than 250 stable isotopes. This allows construction of an enormous number of distinguishable tags. For example, there are 20 distinguishable 3-atom tags that may be constructed from only 4 different isotopes, and one million distinguishable 15-atom tags from 10 different isotopes, or 70-atom tags from 5 different isotopes.
  c) As in a) and b), but incorporating different antibodies with specificity to different target molecules, to allow simultaneous determination of different target molecules. The number of simultaneous determinations is limited by the number of distinguishable tags in combination (which is fewer than the number of distinguishable tags in isolation as described above).

Example 3

Protein A SEPHAROSE Immunoassay

The following provides an example of the methods of the invention using the Protein A SEPHAROSE CL-4B™ (Pharmacia) immunoassay and its protocol. Either NANOGOLD-FAB'™ or another element-labeled Fab' specific to the target protein (or host species of the secondary antibody) may be used. There are two types of immunoassays that may be used, involving analyte complexes:
  a) Direct immunoassay, which would involve trapping the target protein of interest (protein X) by incubating Protein A SEPHAROSE CL-4B™ with an excess of antibody specific to the target protein, washing off the un-reacted antibody, adding the protein sample, washing off the unbound protein, and then exposing the PAS-antibody-protein X complexes to element-labeled, anti-X Fab'.
  b) Indirect immunoassay, which would involve trapping the target protein of interest (protein X) by incubating Protein A SEPHAROSE CL-4B™ with an excess of primary antibody (e.g. polyclonal) specific to the target protein, washing off the unreacted primary antibody, adding the protein sample, washing off the unbound protein, and then exposing the PAS-antibody-protein X complexes to a second antibody specific to protein X (e.g. a monoclonal antibody), washing off un-reacted secondary antibody, and then incubating the PAS-antibody-protein X-antibody complexes with an element labeled, anti-secondary Fab'. Alternatively beads or micro-titer plates covalently bound to anti-protein X antibodies may be used.

PBS buffer A is prepared as follows: 150 mM NaCl; 20 mM phosphate, pH 7.4 ; 1% BSA (bovine serum albumin). All eppendorf tubes, micro-titer plates, and filters, and slurry of Protein A SEPHAROSE CL-4B™ to be used subsequently are pacified with PBS buffer A for 1 hour at room temperature. This treatment will reduce the non-specific interactions that occur between the plastic used and the antigen and NANOGOLD-FAB'™. Alternatively low retention plastic products can be used (e.g. Axygen tubes). Following this a solution of the antigen (peptide, protein, etc.) in the concentration range of 1000 to 0.5 pg/µl in PBS buffer A is prepared. All dilutions are stored on ice. Subsequently, 100 µl of either antigen or PBS buffer A (for controls) is pipetted into the individual wells of the micro-titer plate (or set of eppendorf tubes). The NANOGOLD-FAB'™ is prefiltered through 300 KDa MICRCON™ (or CENTRICON™) centifugal filter devices. Dilutions of filtered NANOGOLD-FAB'™ in PBS buffer A are prepared as follows: A 1:50 dilution is produced by adding 60 μl of NANOGOLD-FAB'™ in 2940 μPBS buffer A. A 1:500 dilution is then produced by adding 100 μof NANOGOLD-FAB'™ to 900 μl of PBS buffer A. Depending on concentration range of antigen, 100 to 500 μl of 1:500 NANOGOLD-FAB'™ is then added to the wells of the plate and then incubated for 1–2 hours at room temperature. The sample is centrifuged at 14,000 rpm for 2 minutes at room temperature. The beads are washed four times with PBS buffer A. In method b) the additional steps to include consist of washing off unreacted monoclonal antibody, and then incubating the PAS-antibody-protein X-antibody complexes with an element-labeled, anti-X Fab'. Finally, a fixed volume of 10% HCl/1 ppbIr is added to each well. Ir provides an internal standard for ICP-MS quantitation and the acid solution is suitable for the elemental analysis.

Figure 2:
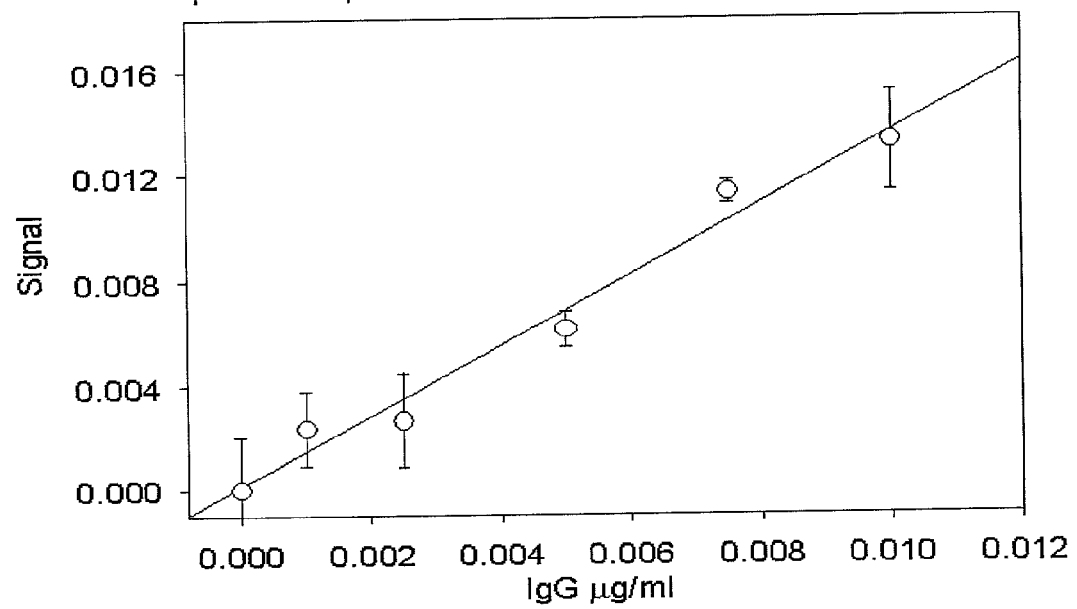
FIG. 2 is graph showing the results of an immunoassay with human IgG and F'ab-Au, over a low concentration range with detection and quantitation using ICP-MS.
Figure 3:
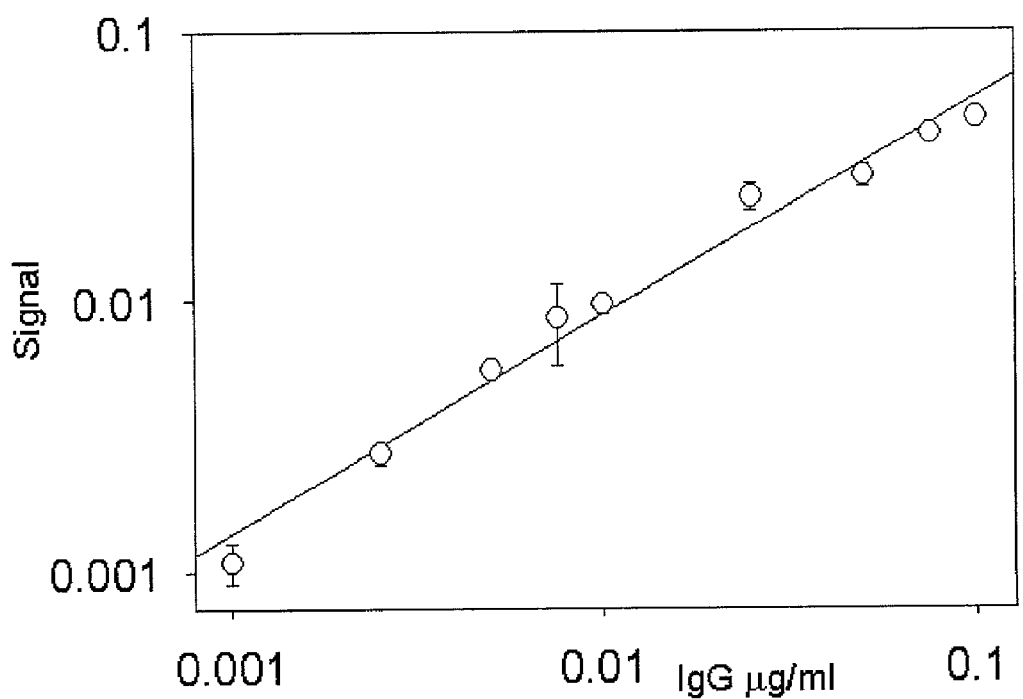
FIG. 3 is a graph showing the results of an immunoassay with human IgG and F'ab-Au, over a high concentration range with detection and quantitation using ICP-MS.

Experimental results obtained according to method a) are given in FIGS. 2 and 3, using human IgG as the analyte with F' ab-Au as the tagged antibody. FIG. 2 provides the calibration results over a relatively low concentration range, and FIG. 3 over a higher concentration range. Together, the data exhibit greater than 2 orders of magnitude of detector linearity with respect to the analyte concentration.

This Example also permits multiplexing to be analyzed and can be used to identify protein-protein interactions. In this method, cell lysate is collected and subjected to the method as above where an interaction is suspected between protein A and protein B. In this case the primary antibody would be specific to protein A and an element-labeled Fab' would be specific to protein B. Interactions with multiple other proteins (e.g. protein C and protein D) could be detected at the same time, providing that different elements were used to label anti-Fab' specific to protein C and anti-Fab' specific to protein D.

Example 4

DYNABEADS™ Immunoassay

The following method provides an example of the invention using the DYNABEADS™ (DYNAL) immunoassay and its protocol. This immunoassay is performed as in Example 3, using DYNABEADS™ in place of Protein A SEPHAROSE CL-4B™. Instead of centrifuging the sample, the sample is exposed to a magnetic device (DYNAL MPC™). This draws the beads to the bottom of the wells between and after each wash step. Again, 10%HCl/1 ppbIr is added to each well in the final step to provide an internal standard for ICP-MS quantitation and elemental analysis.

In the same manner as described for Example 3, multiplexing and protein-protein interactions can be identified using this method.

Example 5

Method for Detection and Quantification of Endogenous Proteins in Cultured Cells.

There are two methods by which the discrete changes in the levels of endogenous proteins in culture cells can be measured.
 a) Direct immunoassay, in which an antibody specific to the protein of interest is required. This antibody is labeled with an element suitable for analysis by ICP-MS.
 b) Indirect immunoassay, in which an analyte complex is formed, whereby an antibody (primary antibody) specific to the protein of interest is required. In addition a secondary antibody specific to the primary antibody is labeled with an element suitable for analysis by ICP-MS.

A mono-layer of attached cultured cells is grown and treated with conditions of interest. The growth media is removed and the cells are washed with 1×PBS three times. PBS is then replaced with ice-cold methanol and the culture dishes are incubated at −20° C. for 5 minutes. The methanol is removed and the cells are allowed to dry completely. A blocking buffer (e.g. 10% horse serum, 1% BSA, 0.05% TWEEN-20, 1×PBS) is added to the culture dishes and the dishes are incubated for 1–2 hours at room temperature. In method a) an antibody specific to the protein of interest is labeled with an element, diluted in blocking buffer and added to the culture dishes. The cells are exposed to the antibody mix for 2 hours at room temperature (or 37° C.). The trademark TWEEN-20 refers to a surfactant, namely p lyoxyethylene sorbitan monolaureat, n ca. 20. During this time, the element-tagged antibody binds the target protein through its tail. In method b) the antibody specific to the protein of interest is not labeled. In the next step, the un-reacted primary antibody is washed away with blocking buffer. In method b) the element-labeled secondary antibody is diluted in blocking buffer and applied to the cells. The dishes are incubated for 1–2 hours at room temperature. The un-reacted secondary antibody is then washed away with blocking buffer. Finally, in both methods, an acid solution (e.g. concentrated HCl) is added, to release and dissolve the tagging element. The dissolved element in acid is diluted with 10% HCl/1ppbIr to provide an internal standard. The acid solution containing the tagging element is then analyzed by ICP-MS to quantify the protein of interest.

Figure 4:
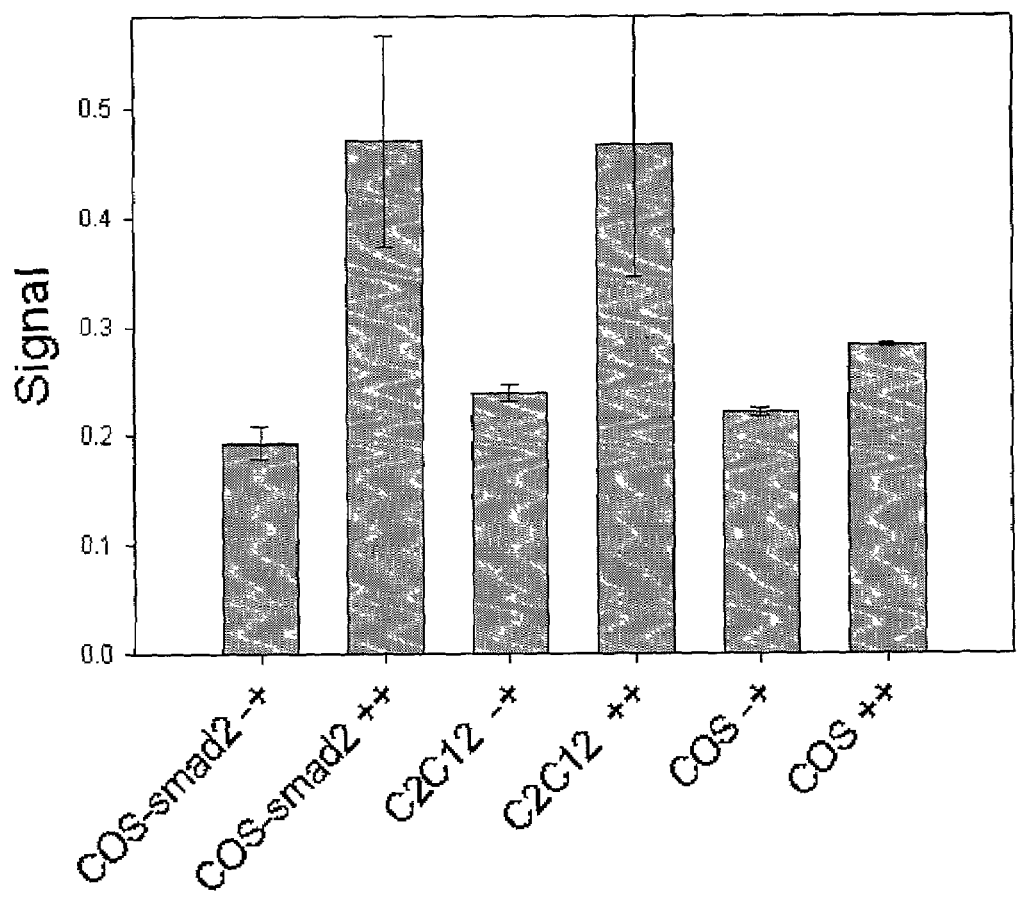
FIG. 4 is a bar graph showing the results of measuring endogenous protein in cultured cells with detection and quantitation using ICP-MS.

Experimental data obtained according to method b) is shown in FIG. 4. This data examines the sensitivity of this immunoassay, by comparing the relative amounts of Smad2 in three different cell cultures; COS (Bars 5 and 6), COS transfected with pCMV5B-Smad2 (COS-smad2) (Bars 1 and 2), and C2C12 cells (Bars 3 and 4). COS cells are known to have undetectable levels of Smad2 protein (using Western blot analysis). Conversely, Smad2 is detectable in C2C12 cell lysate and in COS cells that have been transfected with pCMV5B-Smad2. These cell cultures are prepared in 60 mm dishes, fixed with methanol, blocked with TBST buffer and then incubated in either the presence (Bars 2, 4, and 6) or absence (Bars 1, 3, and 5) of polyclonal anti-Smad2 antibody (Upstate Biotech). Cells are incubated with a gold-tagged anti-rabbit antibody (Nanoprobes), dissolved in concentrated HCl, diluted 2 fold in 10% HCl/1ppbIr and analyzed using the ICP-MS. Each bar is an average of triplicate samples. Bars 1, 3, and 5 reflect negative control cultures not treated with primary antibody (+−). Cultures treated with both primary and secondary antibodies (++) show that in the two cell cultures that express smad2, a substantial increment in the signal over the (−+) results indicates the presence of the smad2 protein. The third culture, COS, which is not expected to express smad2, shows a signal for the (++) case that is roughly comparable to that of the blank (−+).

Example 6

Method for determination efficiency of cell transfection.

The effectiveness of cell culture transfection is determined by first modifying cells to transduce a tail (e.g.

FLAG™). As in Example 5, there are two methods by which the antigen of interest can be detected (directly and indirectly).
  a) Direct immunoassay, in which an antibody specific to the tail is required. This antibody is labeled with an element suitable for analysis by ICP-MS.
  b) Indirect immunoassay, in which an antibody (primary antibody) specific to the tail is required. In addition a secondary antibody specific to the primary antibody is labeled with an element suitable for analysis by ICP-MS. This is another example whereby analyte complexes are used.

Between 1–3 days after transfection of the cells, the growth media (typically 10% FBS, depending on cell-type) is removed and the mono-layer of attached cells are washed with 1×PBS three times. PBS is replaced with ice-cold methanol and the culture dishes are incubated at –20° C. for 5 minutes. The methanol is removed and the cells are allowed to dry out completely. A blocking buffer (e.g. 10% horse serum, 1% BSA, 0.05% TWEEN-20, 1×PBS) is added to the culture dishes and the dishes are incubated for 1–2 hours at room temperature. In method a) an antibody specific to the tail is produced and labeled with an element that is suitable for analyzing with the ICP-MS. The antibody is diluted in blocking buffer and added to the culture dishes. The cells are exposed to the antibody mix for 2 hours at room temperature (or 37° C.). During this time, the element-tagged antibody binds the target protein through its tail. In method b) the antibody specific to the protein of interest is not labeled. The un-reacted primary antibody is washed away with blocking buffer. In method b) the element-labeled secondary antibody is diluted in blocking buffer and applied to the cells. The dishes are incubated for 1–2 hours at room temperature. The un-reacted secondary antibody is washed away with blocking buffer. Finally, in both methods, an acid solution (e.g. concentrated HCl) is added, to release and dissolve the tagging element. The dissolved element in acid is diluted with 10% HCl/1 ppb Ir to provide an internal standard. The acid solution containing the tagging element is analyzed by ICP-MS to quantify the efficiency of the transfection. Culture dishes containing non-transfected cells cultured at the same time can be used as a negative control An alternate variation of this Example involves using a 6×HIS-TAGGED CONSTRUCT™ (Invitrogen), where there is no need for specific antibodies. Cells transfected with 6×HIS-tagged constructs are fixed with methanol, blocked with the blocking buffer and incubated for 2 hours with a solution containing nickel (e.g. Ni-NTA™; Qiagen). The cells are washed to remove free nickel, acid degraded, and analyzed using ICP-MS for nickel content.

Example 7

Reporter Assay

In the study of transcription factors, it is necessary to quantitate the levels of transcription. There are two methods by which discrete changes in the levels of transcription activity on a specific promoter (or enhancer elements) can be measured. Cultured cells are transfected with expression plasmids of interest along with equal amounts of plasmid containing the promoter of interest linked to a reporter gene (e.g. GFP). As in Example 5 there are two methods by which the antigen of interest can be detected (directly and indirectly).
  a) Direct immunoassay, in which an antibody specific to the reporter is required. This antibody is labeled with an element suitable for analysis by ICP-MS.
  b) Indirect immunoassay, in which an antibody (primary antibody) specific to the reporter is required. In addition a secondary antibody specific to the primary antibody is labeled with an element suitable for analysis by ICP-MS.

Cultured cells are grown and transfected with conditions of interest. Upon analysis, the growth media is removed and the cells are washed with 1×PBS three times. PBS is replaced with ice-cold methanol and the culture dishes are incubated at –20° C. for 5 minutes. The methanol is removed and the cells are allowed to dry out completely. A blocking buffer (e.g. 10% horse serum, 1% BSA, 0.05% TWEEN-20, 1×PBS) is added to the culture dishes and the dishes are incubated for 1–2 hours at room temperature. In method a) an antibody specific to the reporter is labeled with an element, diluted in blocking buffer and added to the culture dishes. The cells are exposed to the antibody mix for 2 hours at room temperature (or 37° C.). During this time, the element-tagged antibody will bind the reporter. In method b) the antibody specific to the reporter is not labeled. In the next step, the un-reacted antibody is then washed away with blocking buffer. In method b) the element-labeled secondary antibody is diluted in blocking buffer and applied to the cells. The dishes are incubated for 1–2 hours at room temperature. The un-reacted antibody is then washed away with blocking buffer. Finally, in both methods, an acid solution (e.g. concentrated HCl) is added, to release and dissolve the tagging element. The dissolved element in acid is diluted with 10% HCl/1 ppb Ir to provide an internal standard. The acid solution containing the tagging element is analyzed by ICP-MS to quantify the protein of interest.

Example 8

Detection of Proteins after Electrophoresis using Tagged Antibodies.

A sample of proteins is diluted in 2×SDS sample buffer (1% SDS, 2% glycerol, 100 mM Tris, pH6.8, 5% β-mercaptoethanol, 1% DTT, 1% PMSF, 0.2% leupeptin, 0.2% pepstatin) and exposed to electrophoresis on a 2-D or polyacrylamide gel (SDS-PAGE or N-PAGE) to separate the proteins. The proteins from the gel are transferred to nitrocellulose using a semi-dry transfer apparatus (or equivalent). The nitrocellulose is blocked for 1 hour at room temperature using a blocking buffer (e.g. 5% milk in 1×PBS). An element-tagged antibody that recognizes the target protein is added to blocking buffer and the nitrocellulose blot is exposed to the antibody-containing buffer for 2 hours at room temperature. Alternatively an un-labeled primary antibody that recognizes the target protein is used to bind the target protein, followed by washes with wash buffer, and then probing with a secondary anti-primary antibody that is labeled with an element. The nitrocellulose blot is washed three times with wash buffer (0.2% NP40 in 1×PBS). The protein in question is analyzed and quantified by laser ablation.

Example 9

Detections of Proteins after Modification with 6×HIS-TAG™ (Invitrogen) and Separation by Electrophoresis.

This Example is similar to Example 8; however, the proteins in the sample are modified prior to electrophoresis so that they have an affinity for an element (e.g. the 6×HIS modification yields affinity to Nickel). The gel or blotting paper containing the separated proteins is washed with a solution containing an element (e.g. Ni) that is bound by the protein modification. The gel or blotting paper is analyzed by laser ablation (or direct excisions) and ICP-MS.

Example 10

Size Exclusion Gel Filtration Immunoassay

In this example, ICP-MS is used to detect the presence of a specific antigen. Accordingly, an antibody is tagged with an element (eg. Au, Eu, Ru, etc.) and is introduced into a sample containing the antigen of interest. The elemental-tagged antibody reacts specifically to the target antigen. The resulting tagged antigen-antibody complex is separated from un-reacted antibody using gel filtration (e.g. HIPREP SEPHACRYL™; Pharmacia) in a running buffer containing 1 ppbIr. The eluate is collected in 0.5 ml increments into a 96 well plate, diluted in acid, and analyzed by ICP-MS.

Figure 5:
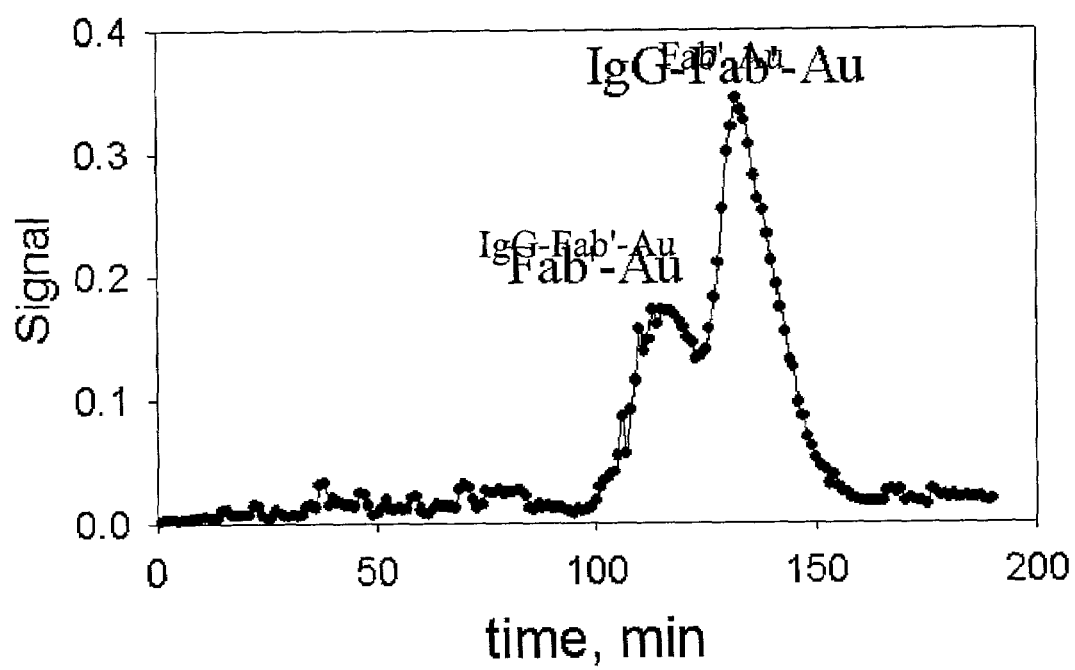
FIG. 5 is a graph showing the detection and quantitation of a specific antigen by ICP-MS.

Experimental results obtained according to this method for IgG analyte using Fab'-Au antibody are shown in FIG. 5. In this experiment an IgG analyte is incubated with an excess of Fab'-Au. The sample is run through a sephacryl S-200 column at a flow rate of 0.5 ml/min, using a running buffer of 0.15M NaCl, 0.02M phosphate, pH 7.4, 1 ppbIr. The figure provides the detector response as a function of elution time (eluate number). The first peak observed (the heavier molecular weight) corresponds to the reacted complex, having an expected molecular weight of about 235 kDa. The second peak corresponds to the unreacted tagged antibody having an expected molecular weight of about 85 kDa.

Example 11

Detection and Quantitation of Elemental Species.

In this example, ICP mass spectrometry is used to measure a quantity of metal identified by an antibody which is specific for a given oxidation state, molecular form or species of a given metal. A target sample containing cationic metal ions is mixed with a molar excess of a metal-free chelator. A high affinity chelator is chosen to ensure that all cationic metal ions in the sample form a complex with the chelator. This solution is then incubated with an antibody, which is specific for the chelator-metal complex. This solution is treated to separate antibody-metal-chelator complexes from un-reacted antibody and the remainder of components in the sample, although it is important only that extraneous metals be removed from the sample.

Preferably, the antibody exhibits little or no ability to bind to the metal-free chelator, and exhibits a tight and specific binding of the metal-complex which is to be measured. Preferably, this binding affinity shows an equilibrium dissociation constant ($K_D$) on the order of $10^{-9}$ to $10^{-8}$M. The antibody used in such assays also is able to resist interference from other components contained in the sample, which is being assayed. The generation of such antibodies may be carried out according to the procedure described in Blake et al. (1998).

The solution containing the antibody-metal-chelator complexes is subject to standard ICP-MS/OES analysis. This approach removes the necessity for a chromatographic pre-separation and consequently improves the sample integrity. It also allows for simultaneous measurement of several metals/oxidation states/elemental species, the method being limited only by the number of antibodies introduced to the sample.

Example 12

Detection and Quantitation of Elemental Species Using Tagged Antibodies.

According to this Example, as in Example 11, antibodies specific for metal-chelator complexes are raised according to methods well known to those skilled in the art. The difference in this Example is the antibody is tagged with multiple atoms of a given tagging isotope, or a stoichiometric mixture of isotopic tags. This has two potential advantages. First, in the event that the target metal element is subject to interference in analysis through typical ICP-based interferences (for example argide ion isobaric interferences) tagging the antibody with a normally non-interfered tag allows for interference-free determination, resulting in improved detectablity. Secondly, specific tags for various species of the same target element allows simultaneous measurement of various species (which would not be provided if the elemental tag were the innate target element itself, since the presence of that element in the spectrum would indicate only that one or more of the target species is present). A further advantage according to this approach is that tagging with multiple atoms of the same isotope allows for signal amplification proportional to the number of atoms of the same tagging isotope.

Example 13

Simultaneous Detection of Numerous Elemental Species in a Sample Using Tagged or Untagged Antibodies.

According to this example, as in Example 11 and 12, antibodies specific for metal-chelator complexes are raised according to methods well known to those skilled in the art. The difference in this Example is that two or more antibodies specific to different elemental species are incorporated, to allow for the simultaneous determination of different speciation states of the same or different elements (where each element is differentially tagged).

Example 14

Immunoassay to Detect Bovine Spongiform Encephalopathy (BSE) in Animal Products.

The methods of Examples 1, 2, 3, 4, 5, 8, and/or 10 are employed to detect BSE in animal products. There are several monoclonal antibodies (15B3, Korth et al., 1997; KG9, Laffling et al., 2001; Bio-Rad Laboratories) that have been produced that target the prion protein PrP thought to be the infectious component responsible for the illness. Monoclonal antibodies specific to PrP are labeled with an element (eg. Au, Eu, Ru, etc.) and used in immunoassays described in either Example 1, 2, 3, 4, 5, 8, and/or 10. Similar products known to be free of BSE would be used as a negative control. In a similar manner other diseases detected for by antibody can be screened for (e.g. HIV, HTLV, Rabies, etc.).

Example 15

Immunoassay to detect ischemic markers in patients believed to have suffered a heart attack The methods of Examples 1, 2, 3, 4, 5, 8, and/or 10 are employed to simultaneously detect multiple ischemic markers in human samples. Candidate markers include: CK-MB, myoglobin, Troponin I, hsp70, BCL2, Bax, IGF, TNFα, angiostatin II.

Example 16

Method for Drug Discovery

In order to aid in drug discovery, animal cells or animal receptors are placed in multi-well plates. The molecule of interest is added (i.e. potential drug), as well as element-tagged antibody (or element tagged ligand) that recognizes the receptor. The potential drug is in competition with the antibody for adhesion to the receptor. Unbound antibody is washed away, and the amount of bound antibody is determined by ICP-MS. This is inversely proportional to the effectiveness of the potential drug to recognize the receptor. If each well is provided with differently labeled antibodies, then by combining the contents of the wells, one can simultaneously assess the effectiveness of various drugs, or drug compositions by deconvoluting the resultant data. Likewise, differently labeled antibodies for the same analyte can be produced and placed in corresponding wells of different plate (i.e. 10 differently labeled version of the antibody, each one placed in well 1, 1 in 10 plates). The plate contents are combined vertically, the reacted antibodies are separated and analyzed simultaneously, with de-convolution to determine the analyte concentration in the corresponding well of each plate.

Example 17

Detection of Tagged Proteins Using 2D Gel and Mass Spectrometry.

In this example, the ICP-DRC-MS technique is used in conjunction with the laser ablation of polyacrylamide gels containing proteins tagged by iron. It is well known that $ArN^+$ and $ArO^+$ interfere with $^{54}Fe^+$ and $^{56}Fe^+$, respectively. To facilitate the method described in Example 11, it is essential to remove isobaric poly-atomic interferences from the iron isotopes. For example, the ratio of the mass spectrometric signals at m/z=54:m/z=56 (where m/z indicates the mass-to-charge ratio of the ion) measured directly by ablation of the polyacrylamide gel containing a protein band tagged by iron was found to be 1.14 (whereas the expected value, based on the natural abundance of the iron isotopes, is 0.063). Utilizing ammonia as a reaction gas in the DRC environment, it is possible to eliminate $ArN^+$ and $ArO^+$ interferences by charge transfer reaction. This approach yielded the m/z=54:m/z=56 ratio that approximated the expected $^{54}Fe^+/^{56}Fe^+$ isotope ratio, by which agreement the determination of the tag iron can be confirmed. In addition, the precision of this measurement is significantly improved due to partial temporal equilibration of ions in the gaseous media of the reaction cell (see Bandura, D. R., et al. 2000).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents, and parent applications are herein incorporated by reference in their entirety to the same extent as if each individual publication, patent or parent application was specifically and individually indicated to be incorporated by reference in its entirety.

What is claimed is:

1. A method for the detection and measurement of a positively charged transition element in a sample, where the measured transition element is a specific tag which is unnaturally bound on an antibody, wherein the antibody binds with an analyte or analyte complex, comprising:
   i) combining the tagged antibody with the analyte or analyte complex, where the tagged antibody binds with the analyte or analyte complex,
   ii) separating the analyte or analyte complex which is bound to the tagged antibody from unbound tagged material, and
   iii) detecting and measuring the positively charged transition element by one of an inductively coupled plasma mass spectrometer and an inductively coupled plasma optical emission spectrometer wherein said transition element is any element having an atomic number of 21–29, 39–47, 57–79 or 89.

2. The method of claim 1 wherein the step ii) includes a step of electrophoresis of the analyte or analyte complex to separate the analyte or analyte complex which is bound to the tagged antibody from the unbound tagged material.

3. The method of claim 1 wherein the analyte complex comprises a primary antibody and an analyte, and wherein the tagged antibody is a secondary antibody tagged with the transition element.

4. A method for the detection and measurement of a transition element in a sample, where the measured transition element is a tag on an antibody, wherein the antibody binds with an analyte or analyte complex, comprising:
   i) combining the tagged antibody with the analyte or analyte complex, where the tagged antibody binds with the analyte or analyte complex,
   ii) separating the bound tagged antibody from unbound tagged material, and
   iii) detecting and measuring the transition element by one of an atomic mass and optical spectrometer having a source of ions or atomic ions; wherein the analyte complex comprises a primary antibody, a secondary antibody and an analyte, and wherein the tagged antibody is a tertiary antibody tagged with the transition element.

5. The method of claim 2 wherein the analyte complex comprises a primary antibody and an analyte, and wherein the tagged antibody is a secondary antibody tagged with the transition element.

6. A method for the detection and measurement of a transition element in a sample, where the measured transition element is a tag on an antibody, wherein the antibody binds with an analyte or analyte complex, comprising:
   i) combining the tagged antibody with the analyte or analyte complex, where the tagged antibody binds with the analyte or analyte complex,
   ii) separating the bound tagged antibody from unbound tagged material by electrophoresis, and
   iii) detecting and measuring the transition element by one of an atomic mass and optical spectrometer having a source of ions or atomic ions; wherein the analyte complex comprises a primary antibody, a secondary antibody and an analyte, and wherein the tagged antibody is a tertiary antibody tagged with the transition element.

7. The method of claim 1 wherein the tagged antibody is an antibody tagged with a nanoparticle having a metal core of 50–70 gold atoms.

8. The method of claim 1 wherein the step of detecting and measuring the positively charged transition element includes an inductively coupled plasma mass spectrometer.

9. The method of claim 1 wherein the transition element is an isotope.

10. The method of claim 1 wherein the transition element is selected from a group consisting of the noble metals, lanthanides, rare earth elements, gold, silver, platinum, rhodium, iridium and palladium.

11. The method of claim 10 wherein the transition element is gold, and wherein the gold has a diameter of 3 nm or less.

12. The method of claim 1 wherein the tagged antibody comprises a covalent coupling of the transition element to the antibody.

13. The method according to claim 1 wherein the antibody is selected from a group consisting of an antigen, hormone, growth factor, receptor, protein and nucleic acid.

14. The method of claim 1 wherein the tag is selected from the group consisting of a plurality of elements, a plurality of isotopes, a plurality of atoms of an isotope, a different number of atoms of each isotope, and combinations thereof, and wherein the step of detecting and measuring comprises detecting and measuring the transition element free of the analyte or analyte complex.

15. The method of claim 1 comprising an additional step of introducing two or more antibodies or analytes having distinguishable elemental tags into a sample of interest for simultaneous determination, and wherein the step of detecting and measuring comprises detecting and measuring the transition element free of the analyte or analyte complex.

16. The method of claim 15 wherein the tag is selected from the group consisting of a plurality of elements, a plurality of isotopes, a plurality of atoms of an isotope, a different number of atoms of each isotope, and combinations thereof, and wherein the step of detecting and measuring comprises detecting and measuring the transition element free of the analyte or analyte complex.

17. The method of claim 1 comprising an additional step of sample introduction to one of the atomic mass and optical spectrometer, wherein the sample introduction includes laser ablation.

18. The method of claim 17 wherein laser ablation is selected from the group consisting of laser ablation of polyacrylamide gels, laser ablation of agarose gels, laser ablation of animal tissue samples, and laser ablation of cell cultures.

19. The method of claim 2 comprising an additional step of sample introduction to one of the atomic mass and optical spectrometer, wherein the sample introduction includes laser ablation of polyacrylamide or agarose gels containing antibodies or analytes tagged with an element selected from the group consisting of at least one element and at least one element having an unnatural composition, and wherein the step of detecting and measuring comprises detecting and measuring the transition element free of the analyte or analyte complex.

20. The method of claim 1 which further comprises a step of running the analyte or analyte complex on an electrophoresis gel prior to the step of combining the tagged antibody with the analyte or analyte complex, to isolate the analyte or analyte complex from the sample.

21. A method for the multiplexed detection and measurement of positively charged transition elements in a sample, wherein the measured transition elements are specific tags, each of which is unnaturally bound on an antibody, and wherein the antibody binds with an analyte or analyte complex, comprising:

i) providing a plurality of antibodies, wherein each antibody of said plurality is tagged with at least one positively charged transition element in a manner that permits a given antibody to be distinguished from other antibodies of said plurality by an inductively coupled plasma spectrometer;

ii) combining said materials with a plurality of analytes and/or analyte complexes, wherein said materials bind with the analyte or analyte complexes in a manner that permits a given analyte or analyte complex to be distinguished from other analytes or analyte complexes by an inductively coupled plasma spectrometer, iii) separating the analytes and/or analyte complexes that are bound to the tagged antibodies from unbound tagged materials, and then iv) detecting and measuring, either simultaneously or sequentially, the positively charged transition elements with an inductively coupled plasma mass spectrometer or an inductively coupled plasma optical emission spectrometer, wherein said transition element is any element having an atomic number of 21–29, 39–47, 57–79 or 89.

22. A method according to claim 21, comprising detecting and measuring with an inductively coupled plasma mass spectrometer.

23. A method according to claim 21, wherein the positively charged transition elements comprise one or more isotopes of positively charged transition elements.

24. A method according to claim 21, wherein the step of detecting and measuring further comprises distinguishing one isotope of a transition element from one or more different isotopes of the same element or from one or more different elements.

25. The method of claim 20 comprising an additional step of introducing two or more antibodies or analytes having distinguishable elemental tags into a sample of interest for simultaneous determination, and wherein the step of detecting and measuring comprises detecting and measuring the transition element free of the analyte or analyte complex.

26. The method of claim 5 comprising an additional step of sample introduction to one of the atomic mass and optical spectrometer, wherein the sample introduction includes laser ablation.

27. The method of claim 6 comprising an additional step of sample introduction to one of the atomic mass and optical spectrometer, wherein the sample introduction includes laser ablation.

* * * * *